(12) United States Patent
Heikenfeld et al.

(10) Patent No.: US 10,646,142 B2
(45) Date of Patent: May 12, 2020

(54) SMART SWEAT STIMULATION AND SENSING DEVICES

(71) Applicant: Eccrine Systems, Inc., Cincinnati, OH (US)

(72) Inventors: Jason Heikenfeld, Cincinnati, OH (US); Gavi Begtrup, Cincinnati, OH (US); Jacob Bertrand, Norwood, OH (US)

(73) Assignee: Eccrine Systems, Inc., Cincinnati, OH (US)

( * ) Notice: Subject to any disclaimer, the term of this patent is extended or adjusted under 35 U.S.C. 154(b) by 690 days.

(21) Appl. No.: 15/186,925

(22) Filed: Jun. 20, 2016

(65) Prior Publication Data

US 2016/0374598 A1 Dec. 29, 2016

Related U.S. Application Data

(60) Provisional application No. 62/185,769, filed on Jun. 29, 2015.

(51) Int. Cl.
| | |
|---|---|
| *A61B 5/145* | (2006.01) |
| *A61B 5/01* | (2006.01) |
| *A61B 5/053* | (2006.01) |
| *A61B 5/00* | (2006.01) |
| *F24V 30/00* | (2018.01) |

(52) U.S. Cl.
CPC ............ *A61B 5/14521* (2013.01); *A61B 5/01* (2013.01); *A61B 5/0533* (2013.01); *A61B 5/4266* (2013.01); *A61B 5/486* (2013.01); *F24V 30/00* (2018.05)

(58) Field of Classification Search
CPC ... A61B 5/14521; A61B 5/486; A61B 5/4266; A61B 5/01; A61B 5/0533; F24V 30/00
See application file for complete search history.

(56) References Cited

U.S. PATENT DOCUMENTS

| | | | |
|---|---|---|---|
| 4,190,060 | A | 2/1980 | Greenleaf et al. |
| 4,542,751 | A | 9/1985 | Webster et al. |
| 4,756,314 | A | 7/1988 | Eckenhoff et al. |
| 4,820,263 | A | 4/1989 | Spevak et al. |

(Continued)

FOREIGN PATENT DOCUMENTS

| | | |
|---|---|---|
| EP | 0282349 A2 | 9/1988 |
| EP | 0453283 A1 | 10/1991 |

(Continued)

OTHER PUBLICATIONS

BurnCentreCare, "About Burned Skin", Nov. 4, 2010, http://burncentrecare.co.uk/about_burned_skin.html.*

(Continued)

*Primary Examiner* — Jacqueline Cheng
*Assistant Examiner* — Abid A Mustansir
(74) *Attorney, Agent, or Firm* — Chad G. Clark

(57) ABSTRACT

The disclosed invention provides sweat sensing devices with smart sweat stimulation and sensing embodiments: which improve the dependability and predictability of sweat sampling rates; achieve a desired number of sweat sampling events per day while minimizing skin irritation and prolonging device lifespan; and use physical, optical or thermal sweat stimulation to augment or replace chemical sweat stimulation.

8 Claims, 3 Drawing Sheets

(56) References Cited

U.S. PATENT DOCUMENTS

| | | | |
|---|---|---|---|
| 5,036,861 A | 8/1991 | Sembrowich et al. | |
| 5,050,604 A | 9/1991 | Reshef et al. | |
| 5,140,985 A * | 8/1992 | Schroeder | A61B 5/14521 |
| | | | 600/323 |
| 5,246,003 A | 9/1993 | Delonzor | |
| 5,437,999 A | 8/1995 | Diebold et al. | |
| 5,438,984 A | 8/1995 | Schoendorfer | |
| 5,556,789 A | 9/1996 | Goerlach-Graw et al. | |
| 5,690,893 A | 11/1997 | Ozawa et al. | |
| 5,814,599 A | 9/1998 | Mitragotri et al. | |
| 5,944,662 A | 8/1999 | Schoendorfer | |
| 6,175,752 B1 | 1/2001 | Say et al. | |
| 6,198,953 B1 | 3/2001 | Webster et al. | |
| 6,256,533 B1 | 7/2001 | Yuzhakov et al. | |
| 6,269,265 B1 | 7/2001 | Anderson | |
| 6,299,578 B1 | 10/2001 | Kurnik et al. | |
| 6,592,529 B2 | 7/2003 | Marett | |
| 6,666,821 B2 | 12/2003 | Keimel | |
| 6,838,480 B1 * | 1/2005 | Wharton | A61K 31/235 |
| | | | 514/53 |
| 7,044,911 B2 | 5/2006 | Drinan et al. | |
| 7,190,986 B1 | 3/2007 | Hannula et al. | |
| 7,219,534 B2 | 5/2007 | Campbell | |
| 7,378,054 B2 | 5/2008 | Karmali | |
| 7,383,072 B2 | 6/2008 | Edmonson et al. | |
| 7,384,396 B2 | 6/2008 | Samuels et al. | |
| 7,749,445 B2 | 7/2010 | Masters | |
| 7,800,494 B2 | 9/2010 | Kim | |
| 7,813,780 B2 | 10/2010 | Shah et al. | |
| 7,842,234 B2 | 11/2010 | Lauks et al. | |
| 7,959,791 B2 | 6/2011 | Kjaer et al. | |
| 8,125,539 B2 | 2/2012 | Takashima | |
| 8,128,889 B2 | 3/2012 | Fujimoto et al. | |
| 8,252,248 B2 | 8/2012 | Kramer | |
| 8,391,946 B2 | 3/2013 | Sugenoya et al. | |
| 8,565,850 B2 | 10/2013 | Martinsen et al. | |
| 8,593,287 B2 | 11/2013 | Hayter et al. | |
| 8,617,067 B2 | 12/2013 | Jain et al. | |
| 9,133,024 B2 | 9/2015 | Phan et al. | |
| 9,867,539 B2 | 1/2018 | Heikenfeld et al. | |
| 2002/0091312 A1 | 7/2002 | Berner et al. | |
| 2003/0135100 A1 | 7/2003 | Kim et al. | |
| 2003/0201194 A1 | 10/2003 | Heller et al. | |
| 2004/0215098 A1 | 10/2004 | Barton et al. | |
| 2004/0249310 A1 | 12/2004 | Shartle et al. | |
| 2004/0260154 A1 | 12/2004 | Sidelnik et al. | |
| 2004/0267189 A1 | 12/2004 | Mavor et al. | |
| 2005/0069925 A1 | 3/2005 | Ford et al. | |
| 2005/0106713 A1 | 5/2005 | Phan et al. | |
| 2005/0177035 A1 | 8/2005 | Botvinick et al. | |
| 2005/0192528 A1 | 9/2005 | Tapper | |
| 2005/0197554 A1 | 9/2005 | Polcha | |
| 2005/0228297 A1 | 10/2005 | Banet et al. | |
| 2005/0280531 A1 | 12/2005 | Fadem et al. | |
| 2006/0009697 A1 | 1/2006 | Banet et al. | |
| 2006/0062852 A1 | 3/2006 | Holmes | |
| 2006/0127964 A1 | 6/2006 | Ford et al. | |
| 2006/0253011 A1 | 11/2006 | Edmonson et al. | |
| 2006/0254341 A1 | 11/2006 | Campbell | |
| 2007/0027383 A1 | 2/2007 | Peyser et al. | |
| 2007/0032731 A1 | 2/2007 | Lovejoy et al. | |
| 2007/0179371 A1 | 8/2007 | Peyser et al. | |
| 2008/0015494 A1 | 1/2008 | Santini, Jr. et al. | |
| 2008/0045816 A1 | 2/2008 | Jang et al. | |
| 2008/0080166 A1 * | 4/2008 | Duong | H01L 33/20 |
| | | | 362/84 |
| 2008/0154179 A1 | 6/2008 | Cantor et al. | |
| 2008/0286349 A1 | 11/2008 | Nomoto et al. | |
| 2008/0306362 A1 | 12/2008 | Davis | |
| 2009/0076345 A1 | 3/2009 | Manicka et al. | |
| 2009/0159442 A1 | 6/2009 | Collier et al. | |
| 2009/0204008 A1 | 8/2009 | Beilin | |
| 2009/0270704 A1 * | 10/2009 | Peyser | A61B 5/14521 |
| | | | 600/346 |
| 2010/0044224 A1 | 2/2010 | Kataky | |
| 2010/0063372 A1 | 3/2010 | Potts et al. | |
| 2010/0130843 A1 | 5/2010 | Caceres Galvez et al. | |
| 2010/0132485 A1 | 6/2010 | Erez et al. | |
| 2010/0198521 A1 | 8/2010 | Haick | |
| 2011/0004072 A1 | 1/2011 | Fletcher et al. | |
| 2011/0054273 A1 | 3/2011 | Omoda | |
| 2011/0079521 A1 | 4/2011 | Revol-Cavalier | |
| 2011/0118656 A1 | 5/2011 | Eckhoff et al. | |
| 2011/0178380 A1 | 7/2011 | Chowdhury | |
| 2011/0196283 A1 | 8/2011 | Imran et al. | |
| 2011/0208458 A1 | 8/2011 | Pinter et al. | |
| 2011/0275918 A1 | 11/2011 | Yamashita et al. | |
| 2012/0004570 A1 | 1/2012 | Shimizu et al. | |
| 2012/0028283 A1 | 2/2012 | Hoss et al. | |
| 2012/0119906 A1 | 5/2012 | Kountotsis | |
| 2012/0123220 A1 | 5/2012 | Iyer et al. | |
| 2012/0165626 A1 | 6/2012 | Irina et al. | |
| 2012/0191147 A1 | 7/2012 | Rao et al. | |
| 2012/0209226 A1 | 8/2012 | Simmons et al. | |
| 2012/0229661 A1 | 9/2012 | Sekiguchi et al. | |
| 2012/0277697 A1 | 11/2012 | Haghgooie et al. | |
| 2012/0285829 A1 | 11/2012 | Mount et al. | |
| 2012/0317430 A1 | 12/2012 | Rahman et al. | |
| 2013/0006079 A1 | 1/2013 | Feldman et al. | |
| 2013/0010108 A1 | 1/2013 | Hashizume et al. | |
| 2013/0013028 A1 | 1/2013 | Kriksunov et al. | |
| 2013/0053668 A1 | 2/2013 | Lin | |
| 2013/0079605 A1 | 3/2013 | Bandaru et al. | |
| 2013/0099937 A1 | 4/2013 | Azimi | |
| 2013/0108667 A1 | 5/2013 | Soikum et al. | |
| 2013/0123595 A1 | 5/2013 | Currie et al. | |
| 2013/0183399 A1 | 7/2013 | Blow et al. | |
| 2013/0245388 A1 | 9/2013 | Rafferty et al. | |
| 2013/0306491 A1 | 11/2013 | Briman et al. | |
| 2013/0317318 A1 | 11/2013 | Tartz et al. | |
| 2013/0317333 A1 | 11/2013 | Yang et al. | |
| 2014/0012114 A1 | 1/2014 | Zevenbergen et al. | |
| 2014/0025000 A1 | 1/2014 | Currie et al. | |
| 2014/0206977 A1 | 7/2014 | Bahney et al. | |
| 2014/0221792 A1 | 8/2014 | Miller et al. | |
| 2014/0275862 A1 | 9/2014 | Kennedy | |
| 2014/0276220 A1 | 9/2014 | Briscoe et al. | |
| 2014/0343371 A1 | 11/2014 | Sowers, II et al. | |
| 2015/0057515 A1 | 2/2015 | Hagen et al. | |
| 2015/0112164 A1 | 4/2015 | Heikenfeld et al. | |
| 2015/0112165 A1 | 4/2015 | Heikenfeld | |
| 2015/0289820 A1 | 4/2015 | Miller et al. | |
| 2016/0058354 A1 | 3/2016 | Phan et al. | |
| 2016/0066828 A1 | 3/2016 | Phan et al. | |
| 2016/0157768 A1 | 6/2016 | Braig et al. | |
| 2016/0256055 A1 * | 9/2016 | Okamura | A61B 5/01 |
| 2017/0100035 A1 | 4/2017 | Heikenfeld | |
| 2017/0100071 A1 | 4/2017 | Heikenfeld | |
| 2017/0215773 A1 | 8/2017 | Heikenfeld et al. | |

FOREIGN PATENT DOCUMENTS

| | | | |
|---|---|---|---|
| EP | 1575010 A1 | 9/2005 | |
| EP | 1637889 A1 | 3/2006 | |
| EP | 2551784 A1 | 1/2013 | |
| EP | 2783725 A1 | 10/2014 | |
| WO | 1990011519 A1 | 10/1990 | |
| WO | 1994014062 A1 | 6/1994 | |
| WO | 2000014535 A1 | 3/2000 | |
| WO | 2001088525 A1 | 11/2001 | |
| WO | 2006133101 A2 | 12/2006 | |
| WO | 2007097754 A1 | 8/2007 | |
| WO | 2007146047 A1 | 12/2007 | |
| WO | 2008058014 A2 | 5/2008 | |
| WO | 2008083687 A1 | 7/2008 | |
| WO | 2008095940 A1 | 8/2008 | |
| WO | 2009004001 A1 | 1/2009 | |
| WO | 2009052321 A2 | 4/2009 | |
| WO | 2010017578 A1 | 2/2010 | |
| WO | WO 2010130861 A1 * | 11/2010 | |
| WO | 2011008581 A2 | 1/2011 | |
| WO | 2011117952 A1 | 9/2011 | |
| WO | 2013111409 A1 | 8/2013 | |
| WO | 2013181436 A1 | 12/2013 | |

(56) References Cited

FOREIGN PATENT DOCUMENTS

| | | |
|---|---|---|
| WO | 2014001577 A1 | 1/2014 |
| WO | 2014025430 A3 | 5/2014 |
| WO | 2015058065 A1 | 4/2015 |
| WO | 2016007944 A2 | 1/2016 |
| WO | 2016049019 A1 | 3/2016 |
| WO | 2016090189 A1 | 6/2016 |
| WO | 2016130905 A1 | 8/2016 |
| WO | 2016138087 A1 | 9/2016 |
| WO | 2017019602 A1 | 2/2017 |
| WO | 2017070640 A1 | 4/2017 |

OTHER PUBLICATIONS

Schweber, Bill, "What . . . You're Using Lasers for Area Heating?", Feb. 16, 2015, https://www.eetimes.com/author.asp?section_id=36&doc_id=1325651.*

Farzana Abanty, "Temperature of a Healthy Human (Skin Temperature)", Aug. 10, 2001, https://hypertextbook.com/facts/2001/AbantyFarzana.shtml.*

International Searching Authority, Search Report issued in corresponding International Application No. PCT/US2016/43771 dated Dec. 8, 2016, 4 pages.

International Searching Authority, Written Opinion issued in corresponding International Application No. PCT/US2016/43771 dated Dec. 8, 2016, 9 pages.

International Searching Authority, Search Report and Written Opinion issued in corresponding International Application No. PCT/US2016/58356 dated Jan. 6, 2017, 15 pages.

International Searching Authority, Search Report and Written Opinion issued in corresponding International Application No. PCT/US2016/58357 dated Jan. 19, 2017, 9 pages.

International Searching Authority, Search Report and Written Opinion issued in corresponding International Application No. PCT/US2017/047808 dated Nov. 6, 2017, 10 pages.

* cited by examiner

SMART SWEAT STIMULATION AND SENSING DEVICES

CROSS-REFERENCE TO RELATED APPLICATIONS

The present application has specification that builds upon U.S. Provisional Application No. 62/185,769, filed Jun. 29, 2015, and PCT/US16/19282 filed Feb. 24, 2016, the disclosures of which are hereby incorporated herein by reference in their entirety.

BACKGROUND OF THE INVENTION

Sweat sensing technologies have enormous potential for applications ranging from athletics, to neonatology, to pharmacological monitoring, to personal digital health, to name a few applications. Sweat contains many of the same biomarkers, chemicals, or solutes that are carried in blood and can provide significant information enabling one to diagnose illness, health status, exposure to toxins, performance, and other physiological attributes even in advance of any physical sign. Furthermore, sweat itself, the action of sweating, and other parameters, attributes, solutes, or features on, near, or beneath the skin can be measured to further reveal physiological information.

Sweat biosensing applications have largely remained relegated to infant chloride assays for Cystic Fibrosis or illicit drug monitoring patches. This is because the majority of medical literature on sweat biomarkers relies on a slow and inconvenient process of sweat stimulation, collection of a sample, transport of the sample to a lab, and then analysis of the sample by a bench-top machine and a trained expert. This process is so labor intensive, complicated, and costly that a blood draw is usually a superior testing modality, since it is the gold standard for most high performance biomarker sensing. Hence, sweat sensing has yet to realize its full biosensing potential, especially for continuous or repeated biosensing. Furthermore, attempts to use sweat sensing to measure "holy grails" like glucose have thus far failed to produce viable commercial products, reducing the perceived capability and opportunity space for sweat sensing.

Among the physiological fluids used for bio monitoring (e.g. blood, urine, saliva, tears), sweat has arguably the least predictable sampling rate in the absence of technology. However, with proper application of technology, sweat can be made to outperform other non-invasive or less invasive biofluids in predictable sampling. For example, it is difficult to control saliva or tear rate without negative consequences for the user (e.g., dry eyes, tears, dry mouth, or excessive saliva while talking). Urine is also a difficult fluid for physiological monitoring, because it is inconvenient to take multiple urine samples, it is not always possible to take a urine sample when needed, and control of biomarker dilution in urine imposes further significant inconveniences on the user or test subject.

By contrast, as disclosed in herein, sweat may be stimulated and sampled when needed, and sweat rates may be controlled for particular applications. For instance, some biomarkers diffuse into sweat at known rates, and these rates will correspond to a particular sweat rate that allows the biomarker's sweat concentration to optimally correlate to its concentration in blood. (e.g., too high of a sweat rate will dilute a biomarker concentration as the biomarker may not have time to equilibrate by diffusion into sweat). An excellent summary is provided by Sonner, et al. in the 2015 article titled "The microfluidics of the eccrine sweat gland, including biomarker partitioning, transport, and biosensing implications", *Biomicrofluidics* 9, 031301, herein included by reference.

Many of the drawbacks and limitations stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings sweat sensing and stimulating technology into intimate proximity with sweat as it is generated. With the improvements embodied in the current invention, sweat sensing can become a compelling new paradigm as a biosensing platform.

SUMMARY OF THE INVENTION

The disclosed invention provides a sweat sensor device capable of smart sweat stimulation and sensing. The disclosed devices and methods improve the dependability and predictability of sweat sampling rates; achieve a desired number of sweat sampling events per day while minimizing skin irritation; and use physical, optical or thermal sweat stimulation to augment or replace chemical sweat stimulation.

BRIEF DESCRIPTION OF THE DRAWINGS

The objects and advantages of the disclosed invention will be further appreciated in light of the following detailed descriptions and drawings in which.

DEFINITIONS

Figure 1:
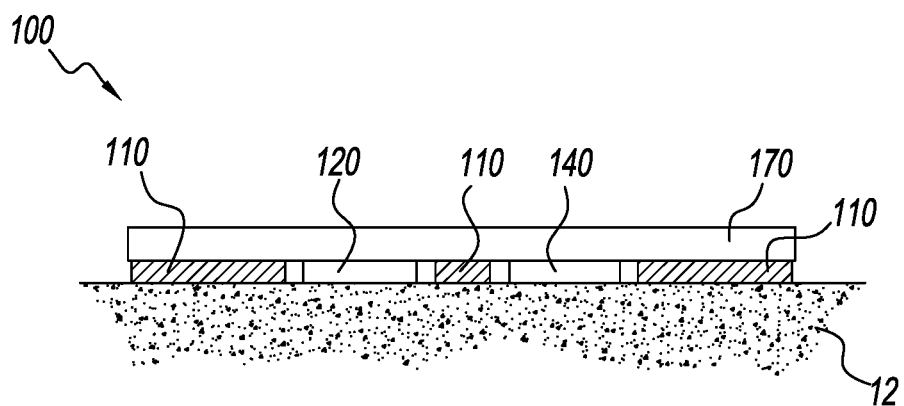
FIG. 1 is a cross-sectional view of at least a portion of a wearable device for sweat biosensing.

"Continuous monitoring" means the capability of a device to collect sweat continuously or in multiple samples and provide at least one measurement of a characteristic of that sweat, or to provide a plurality of measurements of the sweat over time.

"Chronological assurance" means a sampling rate or sampling interval for measurement(s) of sweat, or solutes in sweat, at which measurements can be made of new sweat or its new solutes as they originate from the body. Chronological assurance may also include a determination of the effect of sensor function, or potential contamination with previously generated sweat, previously generated solutes, other fluid, or other measurement contamination sources for the measurement(s).

"Determined" may encompass more specific meanings including but not limited to: something that is predetermined before use of a device; something that is determined during use of a device; something that could be a combination of determinations made before and during use of a device.

"Sweat sampling rate" means the effective rate at which new sweat or sweat solutes, originating from the sweat gland or from skin or tissue, reaches a sensor which measures a property of sweat or its solutes. Sweat sampling rate, in some cases, can be far more complex than just sweat generation rate. Sweat sampling rate directly determines or is a contributing factor in determining the chronological assurance. Times and rates are inversely proportional (rates having at least partial units of 1/seconds), therefore a short or small time required to refill a sweat volume can also be said to have a fast or high sweat sampling rate. The inverse of sweat sampling rate (1/s) could also be interpreted as a "sweat sampling interval". Sweat sampling rates or intervals are not necessarily regular, discrete, periodic, discontinuous, or subject to other limitations. Like chronological assurance, sweat sampling rate may also include a determination of the effect of potential contamination with previously generated sweat, previously generated solutes, other fluid, or other measurement contamination sources for the measurement(s). Sweat sampling rate can also be in whole or in part determined from solute generation, transport, advective transport of fluid, diffusion transport of solutes, or other factors that will impact the rate at which new sweat or sweat solutes reach a sensor and/or are altered by older sweat or solutes or other contamination sources. Sensor response times may also affect sampling rate.

"Sweat stimulation" means the direct or indirect generation of sweat by any external stimulus such as chemical, heat, optical, or other methods, with the external stimulus being applied for the purpose of stimulating sweat. One example of sweat stimulation is the administration of a sweat stimulant such as carbachol, pilocarpine, methylcholine, or other suitable chemical stimulant by iontophoresis, diffusion, injection, ingestion, or other suitable means. Going for a jog, which stimulates sweat, is only sweat stimulation if the individual is jogging for the purpose of stimulating sweat. Sweat stimulation may also include sudomotor axon reflex sweating, where the stimulation site and sweat generation site are not the same but in close in proximity and physiologically linked in the sweat response.

"Sweat stimulating component" means any component or material that is capable of locally stimulating sweat to a rate greater than the natural local rate would be absent such stimulation.

"Sweat generation rate" means the rate at which sweat is generated by the sweat glands themselves. Sweat generation rate is typically measured by the flow rate from each gland in nL/min/gland. In some cases, the measurement is then multiplied by the number of sweat glands from which the sweat is being sampled.

"Measured" may mean an exact or precise quantitative measurement and can include broader meanings such as, for example, measuring a relative amount of change of something. Measured can also mean a binary measurement, such as 'yes' or 'no' type measurements.

"Sweat sensor" means any type of sensor that measures in sweat a state, presence, flow rate, solute concentration, or solute presence, in absolute, relative, trending, or other ways. Sweat sensors can include, for example, potentiometric, amperometric, impedance, optical, mechanical, or other means known by those skilled in the art of sensing or biosensing.

A "sweat sampling event" is a sweat sample that is chronologically assured and represents a meaningful measurement. For a continuous flow of sweat, these events are determined by the sweat sampling rate. For a discontinuous flow of sweat, these events correspond to times when sweat volume or sweat generation rate are adequate to make a proper sweat measurement. For example, if a person needed to measure cortisol 3 times per day, then the sweat generation rate would need to be adequate to provide three sweat sampling events, and other times the sweat generation rate could be higher or lower.

"Sweat threshold temperature" or "sweat onset temperature" means an individual's physiological status relative to sweat generation. Specifically, it is the body or skin temperature at which the individual will sweat adequately so that new sweat reaches a sweat sensor. Sweat thresholds and thermal set points for sweat generation vary from individual to individual, and may also vary from day to day for an individual based on factors like hormone levels, age, external temperature, diet, stressors, responsiveness to sweat stimulation, or other factors. Therefore, the sweat onset temperature for an individual may need to be developed prior to device use, during device use, or may need to be estimated based on the individual's phenotype, age, weight, sex, fitness level, or other relevant factor. Important for these purposes, it is typically easier to generate sweat locally when the body is near or above the sweat onset temperature.

"Diffusion" denotes the net movement of a substance from a region of high concentration to a region of low concentration. This is also referred to as the movement of a substance down a concentration gradient.

DETAILED DESCRIPTION OF THE INVENTION

To better illustrate sweat sampling rate and therefore chronological assurance, this disclosure will first discuss sweat generation rate and sweat volumes. The number of active sweat glands varies greatly among different people, though comparisons between different areas (e.g., axillae versus groin) show the same directional changes (certain areas always have more active sweat glands while others always have fewer). Estimates of the number of glands per $cm^2$ for different areas of the body include: around 370 sweat glands per $cm^2$ for the palm; 200 for the back of the hand; 175 for the forehead; 155 for the chest, abdomen, and forearm; and 60 to 80 for the back and legs. Assuming use of a sweat gland density of $100/cm^2$, a sensor that is 0.55 cm in radius (1.1 cm in diameter) would cover about 1 $cm^2$ area, or approximately 100 sweat glands.

Now, consider some sweat generation rates provided from *Dermatology: an illustrated color text,* 5th ed. The human body excretes a minimum of 0.5 L per day of sweat, has 2.5 million sweat glands on average, and there are 1440 minutes per day. (These values are typically lower for prepubescent children.) Divided among 2.5 million glands, that is rate of 0.2 µL/day/gland or 0.14 nL/min/gland. As another example, the PharmCheck patch, a device that determines the presence of illicit substances, claims the patch collects 2 mL per week, which corresponds to a minimum sweat rate of ~0.1 to 0.2 nL/min/gland in locations with ~100 glands/$cm^2$. Importantly, this number excludes trans-epidermal water loss, which would not provide the solute concentrations that sweat would provide. This is the minimum 'average' sweat generation rate, with some possible exceptions being where sweating naturally increases slightly (such as during sleep cycles, etc.). The maximum sweat generated per person per day is 10 L, which on average is 4 µl, per gland maximum per day, or about 3 nL/min/gland. This is about 20× higher than the minimum sweat generation rate. Both higher and lower rates have been reported and are possible for minimum and maximum sweat rates.

First we return to the assumed sweat gland density of $100/cm^2$, and the 1 $cm^2$ area sensor that covers approximately 100 sweat glands. Next, assume a sweat volume under the sensor (space between the sensor and the skin) of 50 µm average height or 50E-4 cm, and that same 1 $cm^2$ area, which provides a sweat volume of 50E-4 $cm^3$ or about 50E-4 mL or 5 µL of volume. With the maximum sweat generation rate of 5 nL/min/gland and 100 glands, it would require a 10 minutes to fully refresh the sweat volume (using first principles/simplest calculation only). With the minimum sweat generation rate of 0.1 nL/min/gland and 100 glands, it would require 500 minutes, or 8 hours, to fully refresh the sweat volume. If the sweat volume could be reduced by 10× to an effective volume height of roughly 5 µm, the minimum and maximum times required to fully refresh the sweat volume would be 1 minute and 1 hour, respectively, but the minimum time would also be subject to diffusion and other contamination issues (and 5 µm volume height would be technically challenging). Times and rates are inversely proportional (rates having at least partial units of 1/s), therefore a short time required to refill the sweat volume can also be said to have a fast or high sweat sampling rate.

The above examples may be interpreted to provide a chronologically assured sampling interval for sweat, that is, the sampling interval would be the time needed for sweat to fill, or refill, the sweat volume space. Further, because the sweat in the sweat volume space is prone to significant diffusion, mixing, and contamination, such factors may also partially determine sampling interval. The sampling interval could therefore also be more broadly interpreted to include relevant transport, diffusion, or contamination times. It is clear that for many applications, a relatively dependable or predictable sampling rate is required.

In addition to sampling intervals, sweat generation rate per gland may also affect the collection of meaningful physiological information for certain biomarkers. Many biomarker concentrations in sweat exhibit dependence on sweat rate. For example, sweat concentrations of Na+ and Cl— increase with increasing sweat rate because the sweat glands actively generate these ions when producing sweat. Other large or low lipophilic molecules, like cytokines, decrease in concentration as sweat rates increase because these molecules diffuse passively into sweat. At high sweat rates, therefore, there is insufficient time for diffusion to maintain concentrations in sweat that correlate to those in blood. For these molecules, prolonged sweat stimulation at low sweat rates may be necessary. It is clear that for many applications, a relatively dependable or predictable sweat generation rate per gland is required.

The present disclosure applies at least to any type of sweat sensor device that stimulates and measures sweat, sweat generation rate, sweat chronological assurance, its solutes, solutes that transfer into sweat from skin, a property of or things on the surface of skin, or properties or things beneath the skin. The present disclosure applies to sweat sensing devices which can take on forms including patches, bands, straps, portions of clothing, wearables, or any suitable mechanism that reliably brings sweat stimulating, sweat collecting, and/or sweat sensing technology into intimate proximity with sweat as it is generated. Some embodiments utilize adhesives to hold the device near the skin, but devices could also be held by other mechanisms that hold the device secure against the skin, such as a strap or embedding the device in a helmet.

Certain embodiments of the present disclosure show sensors as simple individual elements. It is understood that many sensors require two or more electrodes, reference electrodes, or additional supporting technology or features that are not captured in the description herein. Sensors are preferably electrical in nature, but may also include optical, chemical, mechanical, or other known biosensing mechanisms. Sensors can be in duplicate, triplicate, or more, to provide improved data and readings. Sensors may be referenced herein by what the sensor is sensing, for example: a sweat sensor; an impedance sensor; a sweat volume sensor; a sweat generation rate sensor; a solute generation rate sensor, a galvanic skin response sensor, and so on. Certain embodiments of the invention show sub-components of what would be sweat sensing devices with more sub-components needed for use of the device in various applications, which are obvious (such as a battery), and for purpose of brevity and focus on inventive aspects, are not explicitly shown in the diagrams or described in the embodiments of the disclosure.

Specifically, the present disclosure provides smart sweat stimulation and sensing embodiments, which improve the dependability and predictability of sweat sampling rates; achieve a desired number of sweat sampling events per day while minimizing skin irritation; and use physical, optical or thermal sweat stimulation to augment or replace chemical sweat stimulation.

Sweat stimulation, or sweat activation, can be achieved by known methods. For example, sweat may be stimulated thermally (via infrared light, or a thermal wrap, for example), by orally administering a drug, by intradermal injection of drugs such as carbachol, methylcholine, or pilocarpine, by introduction of a sweat stimulant by diffusion, and by dermal introduction of such drugs using iontophoresis. A device for iontophoresis may, for example, provide direct current into the skin and use large lead electrodes lined with porous material, where the positive pole is dampened with 2% pilocarpine hydrochloride and the negative pole with 0.9% NaCl solution. Sweat can also be controlled or created by asking the device wearer to engage in or increase activities or conditions that cause them to sweat. Other sweat stimulants and stimulation techniques are also possible and known in the art.

The sweat sensor device may be configured to measure sweat rate, for example by using skin impedance or galvanic skin response (GSR), or by measuring Na+, Cl—, and K+ ratios emerging in sweat, or by other means. With a sweat rate measurement, the sweat sensing device may then adjust sweat stimulation to enable a sweat sensing event, or to control for a target sweat generation rate. These techniques may be referred to as active control of sweat generation rate.

In addition to allowing control of sweat generation rates, the disclosed invention also allows sweat stimulation to be applied more efficiently, which may prolong the life of the device through longer battery life or less use of stimulation chemicals. More efficient stimulation also reduces irritation to the wearer's skin that may be caused by the heat, electricity, or chemicals used to stimulate sweat. In general, stimulating sweat when the skin temperature is close to the sweat generation threshold is more efficient than at other times, so the device could be configured to initiate stimulation only when measured skin temperature is naturally close to sweat onset, or the device may instruct the user to increase skin temperature, for example by taking a walk. The device itself may also be configured to increase local skin temperature, for example, by using a thermally insulating layer to seal with the skin around the device. In this way, the seal can create a local environment under the patch with a higher skin temperature in which the sweat glands generate sweat more easily than they would outside the patch. In some cases, this may eliminate the need for any further stimulation. In other cases, it should reduce the amount of stimulation required.

In some embodiments, a device utilizing both a thermal stimulation means, such as an infrared light source, and a chemical stimulation means, such as carbachol or pilocarpine, may provide improved efficiency and reduced skin irritation, e.g., by allowing each means to operate for shorter duration or at lower intensity. Combined use may also allow improved operation on other measures, for example by allowing the sweat sensor device to generate sweat from a lower sweat onset temperature, or by providing redundancy in the event that either means malfunctions, or the skin stops responding to one form of stimulation or the other.

With reference to FIG. 1, a sweat sensing device 100 is placed on or in proximity to skin 12 in order to provide an adequate number of sweat sampling events. The device includes at least one sweat sensor 120, adhesive 110, and at least one sweat stimulating component 140. The device further includes a thermally insulating component 170, effective to cause the local skin temperature under the device to elevate and remain higher than the temperature of skin outside of the device. Raising local skin temperature can increase the affected glands' likelihood of generating sweat, for example, by bringing the glands closer to their sweat generation threshold or sweat onset threshold such that sweat is more easily generated by: (1) natural sweat stimulating events such as exercising, undergoing sleep cycles, drinking a hot beverage, wearing warm clothing, or other natural stimulation methods; or (2) sweat stimulation by the sweat stimulating component 140. The thermally insulating component could be aluminized mylar, an aerogel, a thick textile, or other suitable material capable of raising the local skin temperature by at least 1° C.

Figure 2:
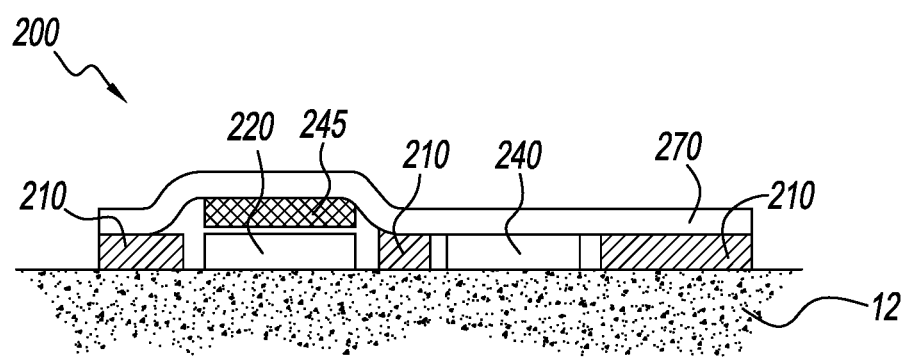
FIG. 2 is a cross-sectional view of at least a portion of a wearable device for sweat biosensing.

With reference to FIG. 2, where like numerals refer to like components or materials depicted in the previous figure, a device 200 includes a thermal sweat stimulation component 245 placed on a sweat sensor 220 on the side opposite skin 12. The thermal stimulation component 245 could be, for example, at least one of the following heater types: a resistive heater, a light emitting diode, or an exothermic chemical reaction material (like that used in hand warmers). Thermal stimulation component 245 and a chemical stimulation component 240 can work in concert to provide an adequate number of sweat sampling events. As an example, stimulation component 240 would use a chemical stimulant such as carbachol.

Figure 3A:
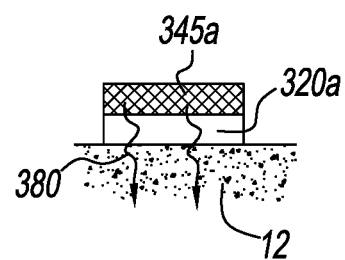
FIGS. 3A to 3C are cross-sectional views of at least a portion of the device of FIG. 2, showing alternate configurations and embodiments.
Figure 3B:
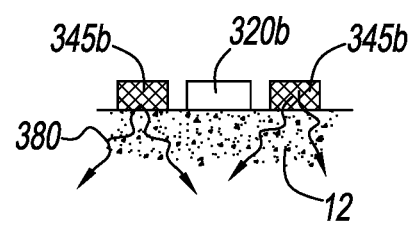
Figure 3C:
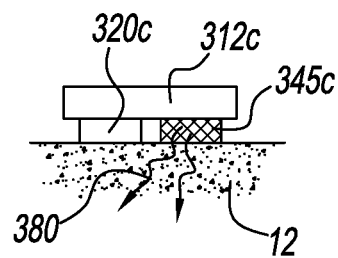

FIGS. 3A to 3C, where like numerals refer to like components or materials of previous figures, depict alternate configurations of sweat stimulation component 245 and sensor 220 for the partial device depicted in FIG. 2. In each FIG. 3 variation, thermal stimulation component 345a, 345b, 345c may optionally be configured as a light source, with light emissions depicted as arrows 380. Light stimulation has a number of advantages over other thermal stimulation modalities, including: deeper absorption into the skin; more directional control (and therefore potentially more efficient delivery to a particular site); easier rapid pulsing; and smaller component size. Skin penetration depths (depth at which only 37% of the original light intensity remains) are several millimeters for visible and near-infrared wavelengths. Light sources for such components may include any type of inexpensive and compact light source, that enables precise control of the radiation direction and pattern, for example an LED, or a laser. Light sources can use lenses, mirrors, or other components to improve directional control, including, for example, achieving a solid cone angle of <45° for >50% of the emitted light, using techniques known by those skilled in the art of optics. With reference to FIG. 3C, both the thermal sweat stimulation component 345c and sweat sensor 320c may be fabricated on a common substrate 312c, such as a polyamide or polyester film.

Figure 4:
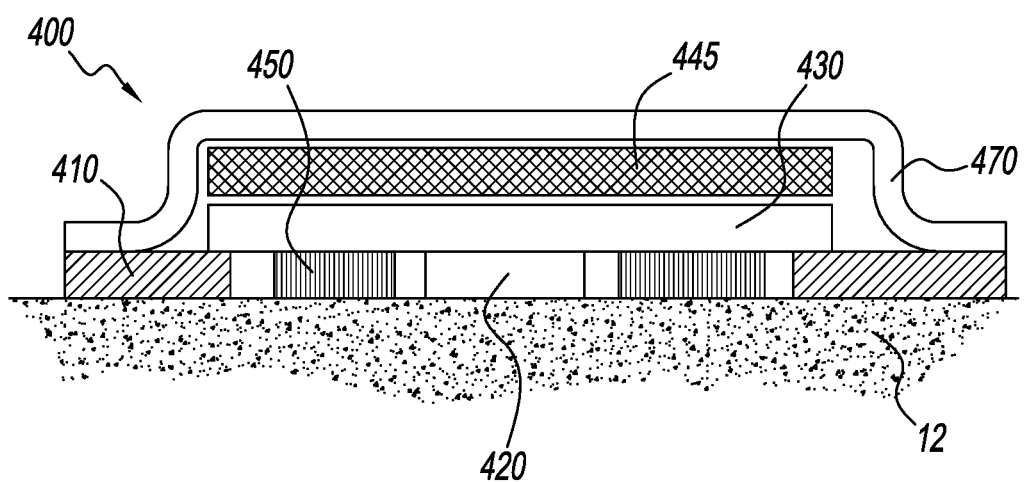
FIG. 4 is a cross-sectional view of at least a portion of a wearable device for sweat biosensing.

With reference to FIG. 4, a partial sweat sensing device is depicted with a chemical sweat stimulating component 450, a thermal sweat stimulating component 445, and a thermally insulating component 470. The thermal sweat stimulating component 445 may be, for example, a material producing a continuous exothermic chemical reaction, such as that used in hand-warmers, which would locally raise the skin temperature and allow increased sweat sampling events. In some embodiments, component 450 may include a chemical numbing agent, such as lidocaine or hydrocortisone, to reduce any physical sensation the user perceives from the sweat stimulation.

The following examples are provided to help illustrate the disclosed invention, and are not comprehensive or limiting in any manner.

Example 1

An individual wears a sweat sensing device similar to that depicted in FIG. 1 to measure their sweat cortisol level on a once-daily basis. The device is configured to allow multiple sampling events to occur naturally during the day, if available, but must conduct at least one chronologically assured sweat sample each day. The device is further configured with skin impedance electrodes and sweat chloride ionophore sensors to determine if a sampling event occurs. If the individual goes through the majority of the day and the device determines by a means like skin impedance, GSR, or sweat chloride concentration, that no chronologically assured sampling event has occurred, the device activates the sweat stimulating component to ensure the required one sampling event occurs.

Example 2

A particular sweat sensor application requires four sweat sampling events per day, at an interval of at least two hours between sampling events. Using continual thermal stimulation to support the application would be ineffective, either because the body may adapt to the thermal stimulation by reducing the sweat response, because continuous thermal stimulation would cause excessive skin irritation, or because such stimulation would be an excessive drain on electronic power or onboard stimulant resources. The sweat sensing device could determine the sweat onset temperature directly by skin impedance, or indirectly by room temperature, heart rate, or other means. Alternately, the device may infer through the individual's behavior that they will soon reach sweat onset, for instance, because the individual is taking a walk. The device also measures when the skin under the device is adequately close to sweat onset via skin temperature, GSR, skin impedance, or other means. Once the skin is sufficiently close to the sweat onset, the device stimulates sweat to allow a sweat sampling event to occur. The amount of needed sweat stimulation varies widely, and by non-limiting example could be 1 minute of carbachol iontophoresis, 1 minute of pulsed LED thermal stimulation, or 15 minutes or more of thermal stimulation. The device may have access to, or may develop, a data profile on the individual's responsiveness to sweat stimulation techniques, duration, intensity, amounts, etc., to determine the most efficient sweat stimulation for the individual. The same technique provides value for chemical or other stimulation methods as well. This embodiment generally describes a sweat sensing device that is opportunistic in terms of when to stimulate, sample and sense sweat. Meaning, that it initiates sweat stimulation when it will use the least resources, and cause the least irritation to the wearer.

Example 3

An individual wearing a sweat sensing device has not yet provided adequate sweat sampling events to enable a particular application. The device communicates to a smart phone, which in turn alerts the user to do something to increase proximity to sweat onset, or alternatively, the device may initiate thermal or chemical sweat stimulation, so that a sweat sampling event can occur. Both inducing sweat directly and improving proximity to sweat onset temperature are distinct embodiments of the disclosed invention. The individual responds to the alert by taking a brisk walk, turning up the room temperature, putting on a sweater, drinking a cup of tea, or other means, to cause a sampling event to occur, or to cause a sweat sampling event to occur by acting in combination with other sweat stimulation techniques. The individual may also orally ingest a chemical sweat stimulant, or other drugs, e.g., pilocarpine, or cevimeline. This embodiment generally describes a sweat sensing device that allows both an opportunistic sweat stimulation strategy, and a proactive sweat stimulation strategy. Meaning, that it instructs the wearer to undertake action(s) that improve their proximity to sweat onset, or initiates artificial sweat stimulation.

Example 4

Conversely, an individual's sweat generation rate may be too high for a particular application, for example, the detection of a large molecule such as a cytokine (the high sweat rate could make a target analyte very dilute, and thus below sensor detection limits). The sweat sensing device responds by alerting the user that they need to reduce activity, cool themselves, or take other action to lower their sweat generation rate, thereby allowing a meaningful sweat sampling event to occur.

Example 5

For a particular application, a user is sufficiently below their sweat onset so that the thermal stimulation required to induce sweating would be of excessive intensity or duration, for example, high enough to induce discomfort or cause short or long term injury. To avoid discomfort or negative health effects, the device applies thermal stimulation in short pulses that stimulate sweat but do not raise the time-averaged skin temperature sufficiently to cause negative effects. Infrared and visible wavelengths generally have adequate absorption length into skin for thermal stimulation by light, and light-emitting diodes are capable of rapid pulsing. Scientific literature indicates that thermal nerve stimulation to cause sweating is due to a dimensional thermal gradient (dT/dz) or a temporal thermal gradient (dT/dt), for which pulsed thermal stimulation is therefore likely more effective per unit energy or average skin temperature than constant thermal stimulation. See Jansen, E., "Optical stimulation of neural tissue," Medical Bionics Conference, Nov. 23, 2011.

Example 6

A sweat sensing device with an exothermal chemical heat component is configured to stimulate sweat by maintaining a local skin temperature between 100 degrees Fahrenheit (° F.) and 106° F. (temperatures of 107° F. and above correlate with medically-known dangerous fevers and tissue damage). Raising the local skin temperature also increases capillary blood flow to skin and increases the rate of solute diffusion. As disclosed, therefore, thermal sweat stimulation has the additional benefit of increasing the rate of biomarker partitioning into sweat, which may allow shorter sampling intervals or improved solute correlation between sweat and blood.

This has been a description of the disclosed invention along with a preferred method of practicing the invention, however the invention itself should only be defined by the appended claims.

What is claimed is:

1. A method of measuring at least one analyte in sweat with a sweat sensing device, comprising:
    applying a sweat sensing device to a wearer's skin;
    scheduling a plurality of sweat sampling events that are required for an application;
    measuring a sweat generation rate from the wearer's skin;
    determining a sweat onset temperature;
    stimulating sweat if the sweat generation rate is insufficient to provide each of the plurality of sweat sampling events with a sweat sample having a chronological assurance; and
    taking a plurality of sweat analyte readings.

2. The method of claim 1, wherein sweat generation rate is determined by one of the following measurements: GSR, skin impedance, skin conductivity, and concentration of at least one sweat ion.

3. The method of claim 1, further comprising: measuring the wearer's skin temperature and comparing the temperature to a sweat onset temperature prior to stimulating sweat.

4. The method of claim 3, further comprising: stimulating sweat if the wearer's skin temperature is proximate to the sweat onset temperature prior to a time at which a sweat sampling event is scheduled to occur, and sweat generation rate is insufficient.

5. The method of claim 3, further comprising: instructing the wearer to increase skin temperature if the wearer's skin temperature is not proximate to the sweat onset temperature prior to a time at which a sweat sampling event is scheduled to occur, and there is sufficient time for the wearer to raise the skin temperature proximate to or greater than the sweat onset temperature.

6. The method of claim 3, further comprising: stimulating sweat if the wearer's skin temperature is not proximate to the sweat onset temperature prior to a time at which a sweat sampling event is scheduled to occur, and there is insufficient time for the wearer to raise the skin temperature proximate to or greater than the sweat onset temperature, and sweat generation rate is insufficient.

7. The method of claim 3, further comprising: instructing the wearer to decrease skin temperature if the wearer's sweat generation rate is in excess of the sweat generation rate needed to provide a sweat sample for a scheduled sweat sampling event.

8. The method of claim 1, further comprising adjusting sweat stimulation, at least in part, upon a previous response to sweat stimulation by the wearer.

* * * * *